United States Patent
Lee

(10) Patent No.: US 8,986,749 B2
(45) Date of Patent: Mar. 24, 2015

(54) POMEGRANATE EXTRACT HAVING A HIGH ELLAGIC ACID CONTENT, AND USE OF THE POMEGRANATE EXTRACT

(75) Inventor: Hae-Yeon Lee, Gyeongii-Do (KR)

(73) Assignees: Hae-Yeon Lee, Uiwang, Gyeonggi-do (KR); Health-Love Co., Ltd., Hwaseong, Gyeonggi-do (KR)

( * ) Notice: Subject to any disclaimer, the term of this patent is extended or adjusted under 35 U.S.C. 154(b) by 0 days.

(21) Appl. No.: 13/639,026

(22) PCT Filed: Apr. 7, 2011

(86) PCT No.: PCT/KR2011/002453
§ 371 (c)(1),
(2), (4) Date: Oct. 2, 2012

(87) PCT Pub. No.: WO2011/126324
PCT Pub. Date: Oct. 13, 2011

(65) Prior Publication Data
US 2013/0028994 A1 Jan. 31, 2013

(30) Foreign Application Priority Data

Apr. 8, 2010 (KR) .................. 10-2010-0032322
Apr. 8, 2010 (KR) .................. 10-2010-0032329
Jul. 28, 2010 (KR) .................. 10-2010-0072881

(51) Int. Cl.
*A61K 36/185* (2006.01)

(52) U.S. Cl.
CPC ........... *A61K 36/185* (2013.01); *A61K 2236/30* (2013.01)
USPC ......................................... 424/725; 424/777

(58) Field of Classification Search
None
See application file for complete search history.

(56) References Cited

U.S. PATENT DOCUMENTS

2005/0202103 A1* 9/2005 Rajendran et al. ............ 424/702

OTHER PUBLICATIONS

Jimenez et. al. (A New Method of Standartization of Health-Promoting Fruit (*Punica Granatum*) Extract Georgian Medical News vol. 7 (Dec. 31, 2006) pp. 70-76).*
Hyuk Hwa Kim et al., "Estrogenic activity and Physiological Active Components of Iranian Black Pomegranate Seed Extracts," Industrial Food Engineering, vol. 11, No. 4, pp. 305-312 (2007).
Mori-Okamoto, J. et al., "Pomegrate extract improves a depressive state and bone properties in menopausal syndrome model ovariectomized mice," Jrl. of Ethnopharmacology, vol. 92, pp. 93-101 (2004).
del Rio, Jimenez, et al., "A New Method of Standartization of Health-Promoting Pomegranate Fruit (*Punica Granatum*) Extract", Georgian Medical News, vol. 7, (Dec. 31, 2006) pp. 70-76.
Food Engineering Progress, Estrogenic activity and Physiological Active Components of Iranian Black Pomegranate Seed Extracts (Nov. 2007), vol. 11, No. 4, pp. 305-312.
Journal of Ethnopharmacology, Pomegranate extract improves a depressive state and bone properties in menopausal syndrome model ovariectomized mice (Feb. 3, 2004), vol. 92, pp. 93-101.
Viuda-Martos, M. et al., "Pomegranate and its Many Functional Components as Related to Human Health: a Review", Comprehensive Reviews in Food Science and Food Safety, vol. 9, 2010, pp. 635-654.
Wang, R. et al., "Pomegranate: Constitutents, Bioactivities and Pharmacokinetics" Fruit, Vegetable and Cereal Science and Biotechnology, 4 (Special Issue 2), pp. 77-87, 2010.

* cited by examiner

*Primary Examiner* — Chris R Tate
*Assistant Examiner* — Randall Winston
(74) *Attorney, Agent, or Firm* — Mintz Levin Cohn Ferris Glovsky and Popeo, P.C.; Kongsik Kim

(57) ABSTRACT

A pomegranate pulp extract is disclosed. The pomegranate pulp extract is effective in relieving women's menopausal symptoms, anxiety disorders, depression or attention deficit disorders due to the presence of a large amount of ellagic acid. Further disclosed is a method for further improving the relieving effect of the pomegranate extract on women's menopausal symptoms, anxiety disorders, depression or attention deficit disorders. The method includes increasing the content of ellagic acid in the pomegranate extract.

3 Claims, No Drawings

POMEGRANATE EXTRACT HAVING A HIGH ELLAGIC ACID CONTENT, AND USE OF THE POMEGRANATE EXTRACT

CROSS-REFERENCES TO RELATED APPLICATIONS

This application is a U.S. national phase application, pursuant to 35 U.S.C. §371, of PCT/KR2011/002453, filed Apr. 7, 2011, designating the United States, which claims priority to Korean Patent Application No. 10-2010-0032329, filed Apr. 8, 2010, Korean Patent Application No. 10-2010-0032322, filed Apr. 8, 2010, and Korean Patent Application No. 10-2010-0072881, filed Jul. 28, 2010. The entire contents of the aforementioned patent applications are incorporated herein by this reference.

TECHNICAL FIELD

The present disclosure relates to a particular pomegranate extract, a relieving effect of the pomegranate extract on women's menopausal symptoms, anxiety disorders, depression or attention deficit disorders, and a method for improving the efficacy of the pomegranate extract.

BACKGROUND ART

Estrogen as an endocrine hormone is synthesized in vivo from cholesterol and is secreted from ovarian follicles and corpora lutea. When gonadotropins secreted from the anterior pituitary gland transmit signals to reproductive organs, follicle stimulating hormone (FSH) and luteinizing hormone (LH) regulating the menstrual cycle and enabling pregnancy are secreted and act on the ovaries, where estrogen and progesterone are secreted. Estrogen is a generic name for a group of hormones, including estradiol, estrone and estriol.

Ovaries in premenopausal women are main sources of estrogen. As women reach menopause, their aged ovaries are less likely to respond to hypophyseal gonadotropins (follicle stimulating hormone and luteinizing hormone), leading to a further shortening of the early follicular phase. As a result, the menstrual cycle and the ovulatory phase are more shortened, the production of progesterone is reduced, and the cycle is more irregular. Consequently, the ovarian follicles do not respond to hypophyseal gonadotropins, thus failing to produce estrogen any further. The reduced secretion of estrogen can have major effects on a woman's body, including the genitourinary system. Further, when ovulation stops, this leads to menopause, which signifies the end of menstruation, or the hormone reduction before menopause leads to the occurrence of menopausal symptoms.

The rapidly reduced estrogen in postmenopausal women results in increased dangers of psychological and emotional symptoms, for example, fatigue, excitement, sleeplessness, poor concentration, depression, memory loss, headache, anxiety and nervousness. Other possible dangers include fatigue and excitement resulting from sleep disturbance caused by recurrent facial flushing, intermittent dizziness, paresthesia, tachycardia, pyknocardia, nausea, constipation, diarrhea, arthralgia, myalgia, cold hands and feet, and weight gain. Further, postmenopausal women are very susceptible to osteoporosis and cardiovascular diseases, including heart diseases, hypertension and apoplexy, which are associated with an increase in mortality. Furthermore, changes in integumentary and genitourinary systems are caused, and the possibility of the incidence of autoimmune diseases, cataract and colorectal cancer is increased.

The most effective known method for relieving menopausal symptoms, such as facial flushing, is to administer estrogen to women in need of estrogen supplementation.

However, long-term administration of synthetic estrogen may lead to cause serious problems such as the incidence of breast cancer and uterine cancer. Many recent reliable reports have asserted that long-term administration of synthetic estrogen as a hormone replacement therapy increases the possibility of inducing breast cancer. This issue remains highly controversial in all areas of society as well as in research groups. Although the exact cause for the incidence of breast cancer is not clearly demonstrated, the risk of the incidence of breast cancer in women having undergone synthetic estrogen replacement therapy is believed to be associated with estrogen exposure dose with time.

Under these circumstances, considerable research efforts have been directed toward finding phytoestrogen, a kind of vegetable estrogen, as a safer substitute for synthetic estrogen used in hormone replacement therapy. Phytoestrogen refers to a non-steroidal plant compound that exerts estrogenic effects in animals. Most cereals, fruits and vegetables known to have anticancer activity and are effective against heart diseases contain a slight amount of phytoestrogen.

Thus, there is an increasing demand for a safe drug or health functional food that is effective in relieving women's menopausal symptoms without causing diseases such as breast cancer and uterine cancer.

On the other hand, anxiety disorders are defined as mental disorders that involve a feeling of uneasiness without reason or excessive worry. Anxiety disorders refer to conditions that include a feeling of uneasiness or excessive worry even in a situation where there is no need to feel uneasy. Generally, patients with anxiety disorders feel impatient, get stroppy, are very sensitive, and tend to worry about improbable dangers and imagine the worst possible scenario. Physical symptoms of anxiety disorders are rapid heartbeats, indigestion, diarrhea, constipation, perspiration, headache caused by muscle stress, and insomnia. Examples of anxiety disorders include phobic disorders, panic disorders, generalized anxiety disorders, and obsessive compulsive disorders.

Depression is a kind of mental disease that is characterized by a melancholy mood that causes a lack of motivation. Depressed patients feel incapacitated, isolated, futile and guilty and tend to attempt suicide. Depression is one of the most clinically common mental disorders. One out of ten adults experiences depression once or more during his or her lifetime. Representative depression symptoms are melancholy, sadness and uneasiness without any reason, loss of interest in everything, and smilelessness. Depressed patients often wake up during the night and lose their appetite, and reduce their food intake. Depression in people in their forties and fifties is distinguished by nervousness, passion, severe hypochondriacal neurosis, regret, a sense of guilt, despair, paranoidal tendency and depressive delusion, in addition to the major symptoms. These symptoms are mainly found in persons who are compulsive, conscientious, stubborn, responsible, impetuous and sensitive.

Attention deficit disorders, including attention deficit hyperactivity disorder (ADHD), are psychological disorders that are frequently seen in children and adolescents suffering from distraction, hyperactivity, impulsiveness, learning disability, etc. Until the 1970s, attention deficit disorders were known to occur during childhood and last throughout adolescence. Some research reports show that in many cases, attention deficit disorders can continue to last throughout adulthood. Early detection of attention deficit disorders increases the possibility of stopping the occurrence of symptoms in adults. Therefore, early treatment of attention deficit disorders is vitally important.

Anti-anxiety drugs and/or antidepressants are administered to treat anxiety disorders and depression. However, long-term administration of these drugs may cause safety problems. Particularly, care should be taken to avoid dependency on anti-anxiety drugs. Central nervous system stimulants and tricyclic antidepressants are primarily selected drugs for the treatment of attention deficit disorders. However, administration of these drugs is insufficient to obtain the desired effects.

In advanced modern society, the incidence of mental diseases, such as anxiety disorders, depression and attention deficit disorders, is increasing dramatically. In this situation, medicines and/or health functional foods helpful in the treatment of these diseases have been steadily investigated. These diseases are not treated by taking drugs only once or several times but their treatment requires long-term administration of drugs. Thus, there is a need to develop a medicine or a health functional food that is safe in humans despite long-term administration.

DISCLOSURE

Technical Problem

The present disclosure is designed to solve the problems of the prior art, and therefore it is an object of the present disclosure to provide a composition that is effective in relieving women's menopausal symptoms, anxiety disorders, depression or attention deficit disorders.

It is another object of the present disclosure to provide a method for improving the relieving effect of a pomegranate extract on women's menopausal symptoms, anxiety disorders, depression or attention deficit disorders.

Technical Solution

In order to achieve the above objects, the present disclosure provides a pomegranate pulp extract containing ellagic acid in an amount that is effective to relieve women's menopausal symptoms, anxiety disorders, depression or attention deficit disorders.

The content of ellagic acid in the pomegranate pulp extract is preferably at least 0.8 mg/g, more preferably from 0.8 to 1.8 mg/g, even more preferably from 0.8 to 1.4 mg/g.

If the ellagic acid content is less than 0.8 mg/g, the relieving effect of the pomegranate pulp extract on menopausal symptoms, anxiety disorders, depression or attention deficit disorders is negligible. Meanwhile, the ellagic acid content exceeding 1.8 mg/g may increase the risk of side effects, for example, GOT and GPT, which are indicative of liver function, outside their normal ranges.

The present disclosure has been made based on the finding that the use of a pomegranate pulp extract containing a large amount of ellagic acid effectively relieves women's menopausal symptoms, anxiety disorders, depression or attention deficit disorders. Based on this finding, the present disclosure provides a pomegranate extract containing ellagic acid in an amount that is effective to relieve women's menopausal symptoms, anxiety disorders, depression or attention deficit disorders, and a method for further improving the relieving effect of the pomegranate extract on women's menopausal symptoms, anxiety disorders, depression or attention deficit disorders by increasing the content of ellagic acid in the pomegranate extract.

Pomegranate is a plant that grows naturally in Southwest Asia, India's northwest province and California, U.S.A. Pomegranates are widely cultivated in subtropical and tropical regions. From ancient times, pomegranates, particularly red pomegranates, have been known as tonic medicinal materials. Particularly, pomegranates are known to be very effective in preventing hypertension and arteriosclerosis. Pomegranates include water-soluble carbohydrates in amounts as large as 38 to 47% and various kinds of vitamins and minerals.

The kind of pomegranates used in the present disclosure is not particularly limited, but red pomegranates are preferred. Specific examples of red pomegranates include those from Iran, California, Taiwan, Uzbekistan, Turkey and Korea. The content of ellagic acid in the pomegranate extract of the present disclosure may vary depending on the production area and harvest time of the pomegranate used. However, the ellagic acid content of the final extract of the present disclosure is adjusted to a particular range, preferably at least 0.8 mg/g, more preferably from 0.8 to 1.8 mg/g, even more preferably from 0.8 to 1.4 mg/g.

The pomegranate pulp extract of the present disclosure may be prepared, for example, in accordance with the following method. First, pomegranate fruits are washed. The pomegranate pericarps and seeds are completely removed. One or more kinds of enzymes, such as pectinase, proteinase, amylase and cellulase, are added to degrade polysaccharides, such as starch, present in the pomegranate. Thereafter, one or more additives, such as gelatin, silicon dioxide, bentonite, silicasol, tannin, cellulose and potassium casseinate, are optionally added to control the physical properties (e.g., turbidity, color and viscosity) of the pomegranate extract, followed by concentration under heating. The pomegranate extract thus obtained contains a particular amount of ellagic acid.

The pomegranate pulp extract of the present disclosure does not contain ingredients from the pomegranate pericarps and seeds, which may cause side effects. For example, the pomegranate pericarps contain particular kinds of alkaloids that damage the physical functions of humans and negatively affect the respiratory system and muscles. Addiction to the alkaloids may cause side effects such as seizure, convulsion and narcosis. Other side effects are allergic reactions, such as tongue swelling, that may occur in some persons who take pomegranate seed extracts.

The pomegranate pulp extract of the present disclosure contains daidzein, genistein, quercetin, estriol and 17β-estradiol, which are representative ingredients of pomegranate extracts. The contents of these ingredients in the pomegranate pulp extract of the present disclosure are almost identical to those in commercially available pomegranate extract products. However, there is a large difference in the content of ellagic acid between the pomegranate pulp extract of the present disclosure and commercially available products. This difference is assumed to bring about an improvement in the relief of menopausal symptoms. Accordingly, the present disclosure provides a composition containing ellagic acid as an active ingredient that is effective in relieving women's menopausal symptoms, anxiety disorders, depression or attention deficit disorders.

The reason for the higher content of ellagic acid in the pomegranate pulp extract of the present disclosure is assumed to be attributed to the kind of the pomegranate as a raw material, the use of the pulp, particular production conditions (for example, concentration temperature and time conditions (about 55-90° C. (about 1-5 minutes), about 105-110° C. (about 30-150 seconds) and about 100-105° C. (about 30-150 seconds) of the pomegranate extract), etc., but the present disclosure is not limited thereto.

The present disclosure also provides a health functional food for relieving women's menopausal symptoms, anxiety disorders, depression or attention deficit disorders, including the pomegranate pulp extract or ellagic acid as an active ingredient.

In addition to the pomegranate extract, the health functional food of the present disclosure may further include one or more pharmacologically active ingredients and/or additives so long as the objects of the present disclosure are not impaired. Examples of such ingredients and additives include, but are not limited to, *Paeonia japonica, Cornus officinalis, Acanthopanax senticosus, Ganoderma lucidium*, the stem bark of *Fraxinus rhynchophylla, Eucommia ulmoides, Angelica gigas, Gardenia jasminoides, Astragalus membranaceus*, malt, trifoliate orange, vitamin C, fructooligosaccharides, stevioside, purified water, and maltodextrin. These ingredients and additives may be used alone or as a mixture thereof.

For example, the health functional food of the present disclosure may include: water-soluble vitamins, such as thiamine (vitamin $B_1$), riboflavin, ascorbic acid, niacin and vitamin $B_6$; fatty acids, such as myristic acid, palmitic acid, stearic acid, oleic acid and linoleic acid; weak acids, such as glycolic acid and acetic acid; and amino acids, such as 8 essential amino acids, i.e. threonine, valine, methionine, isoleucine, leucine, phenylalanine, tryptophan and lysine, aspartic acid, serine, glutamic acid, proline, glycine, alanine, cysteine, tyrosine, histidine and arginine.

The present disclosure also provides a method for improving the relieving effect of the pomegranate extract on women's menopausal symptoms, anxiety disorders, depression or attention deficit disorders by increasing the content of ellagic acid in the pomegranate extract. In the method of the present disclosure, the content of ellagic acid is preferably adjusted to at least 0.8 mg/g, more preferably 0.8 to 1.8 mg/g, even more preferably 0.8 to 1.4 mg/g.

In one embodiment, a daily dose of the pomegranate pulp extract of the present disclosure is preferably from 0.3 to 1 ml/kg body weight. If the daily dose of the pomegranate pulp extract is less than 0.3 ml/kg body weight, the relieving effect of the pomegranate pulp extract on menopausal symptoms, anxiety disorders, depression or attention deficit disorders is negligible. Meanwhile, the daily dose of the pomegranate pulp extract exceeding 1 ml/kg body weight does not contribute to further improvement in the relief of menopausal symptoms, anxiety disorders, depression or attention deficit disorders when compared to the daily dose of 1 ml/kg weight body. Accordingly, a daily dose of 0.3 to 1 ml/kg weight body is preferred from the view point of in vivo availability and economic efficiency.

According to this embodiment, after the pomegranate pulp extract of the present disclosure is administered daily at a dose of 0.3 to 1 ml/kg body weight, human health indices (for example, red blood cell (RBC) count, blood urea nitrogen (BUN) level, aspartate aminotransferase (AST) level, alanine aminotransferase (ALT) level, creatinine level, glucose level, S-G value, etc.) are maintained within their normal ranges, thus accomplishing the relieving effect of the pomegranate pulp extract on menopausal symptoms, anxiety disorders, depression or attention deficit disorders in a safe manner without causing side effects in humans.

Advantageous Effects

The pomegranate pulp extract of the present disclosure is effective in relieving women's menopausal symptoms, anxiety disorders, depression or attention deficit disorders. In addition, according to the method of the present disclosure, the relieving effect of the pomegranate extract on women's menopausal symptoms, anxiety disorders, depression or attention deficit disorders can be improved.

MODE FOR DISCLOSURE

The present disclosure will be explained in detail with reference to the following examples. However, these examples may be embodied in various different forms and should not be construed as limiting the scope of the present disclosure. The examples are provided to more fully explain the present disclosure to those having ordinary knowledge in the art to which the present disclosure pertains.

EXAMPLES

Example 1

Preparation of Pomegranate Extracts with High Contents of Ellagic Acid

First, foreign matter was removed from pomegranate fruits. Damaged fruits were discarded, and the chosen fruits was washed, cut into pieces, peeled, and pressed under 160 bar to separate the seeds. The pomegranate juice thus obtained was pasteurized. Pectinase was added in an amount of 100-160 g with respect to 6000 L of the pomegranate juice and allowed to stand at 50-60° C. for 1 hr to degrade starch. Gelatin, silicon dioxide and bentonite were added to maintain the turbidity and color of the pomegranate juice and to adjust the viscosity of the pomegranate juice in view of ease of administration. The gelatin and the silicon dioxide were added in amounts of 1200-1800 g and 6000 g, respectively, with respect to 6000 L of the pomegranate juice, and the bentonite was added in an amount of 14 kg with respect to 1000 L of the pomegranate juice. After stirring at 50-60° C. for 30 min, the mixture was filtered under vacuum and concentrated under heating at 55-90° C. for 3 min, 105-110° C. for 90 sec and 100-105° C. for 90 sec to prepare a pomegranate extract containing 0.8-1.4 mg/g of ellagic acid. The pomegranate extract was cooled and pasteurized at 90-94° C. for 20 sec. This procedure was repeated six times. The obtained pomegranate extracts were used as samples in Example 2 below.

Example 2

Evaluation of Ellagic Acid Contents of Pomegranate Extracts

The ellagic acid contents of three commercially available products and the pomegranate extracts prepared in Example 1 (hereinafter also referred to simply as "inventive extracts") were evaluated by the following procedure. The results are shown in Table 1. Six samples with different lot numbers were purchased for each of the commercially available products.

The ellagic acid contents were measured by high-performance liquid chromatography (HPLC). The HPLC was done on an SP C18 UG 120 (4.6 mm×50 mm, 5 μm) as a column using 0.85% phosphoric acid, a mixed solution of distilled water and methanol (6:4), and pure methanol as mobile phases in a gradient separation mode. Ellagic acid was detected using a UV detector at a wavelength of 370 nm.

TABLE 1

| (Unit: mg/g) | Product A | Product B | Product C | Inventive Extracts |
|---|---|---|---|---|
| Sample No. 1 | 0.21 | 0.39 | 0.27 | 0.80 |
| Sample No. 2 | 0.18 | 0.22 | 0.40 | 0.87 |
| Sample No. 3 | 0.46 | 0.08 | 0.21 | 1.01 |
| Sample No. 4 | 0.19 | 0.13 | 0.27 | 1.40 |
| Sample No. 5 | 0.34 | 0.21 | 0.35 | 1.28 |
| Sample No. 6 | 0.32 | 0.19 | 0.37 | 1.09 |
| Ellagic acid content range | 0.18~0.46 | 0.08~0.39 | 0.21~0.40 | 0.80~1.40 |

Products A, B and C in Table 1 were purchased from Shadaab Co., Pashapour Trading Co., and Noosh Iran Co., respectively.

As can be seen from Table 1, the inventive extracts had higher contents of ellagic acid than the commercially available products.

Example 3

Evaluation of Relief of Menopausal Symptoms Depending on Ellagic Acid Content

An evaluation was made as to what extent the pomegranate pulp extracts containing large amounts of ellagic acid prepared in Example 1 relieved women's menopausal symptoms by the following procedure.

Subjects

Through blood tests and Kupperman index, a total of 50 volunteers were publicly selected from postmenopausal women, aged 45-65, who had amenorrhoea of at least 6 months and an FSH value of at least 40. The subjects were divided into 5 experimental groups, 10 subjects per group. Each of the subjects was allowed to take 56 pouches of the pomegranate concentrate over 4 weeks. Specifically, each subject received 20 ml of the pomegranate extract twice daily for 4 weeks. The experimental groups consisted of a control group (70 g of fructooligosaccharide and 13 g of isomerized glucose in purified water), a test group administered with Product A (ellagic acid 0.18-0.46 mg/g), a test group administered with Product B (ellagic acid 0.08-0.39 mg/g), a test group administered with Product C (ellagic acid 0.21-0.40 mg/g), and a test group administered with the inventive extract (ellagic acid 0.8-1.4 mg/g). Each subject was allowed to take the pomegranate extract along with 80 ml of water for mouth rinse.

Test Methods

The tests were conducted for a total of 5 weeks. One week prior to administration of the test extracts, the basic information of the volunteers, such as demographic data and past medical history, were recorded. The nutritive conditions, integumentary/mucosal system, otolaryngology system, cardiovascular system, urogenital system, respiratory system, metabolic/endocrine system, digestive system, musculoskeletal system, nervous/mental system and other physical conditions were medically inspected, and whether the results were normal or not was recorded.

According to general exclusion criteria for Kupperman testing, the following subjects were excluded: subjects who suffered from psychogenic menopausal disorders, who had undergone hormone replacement therapy before at least 6 months of testing or were receiving hormone replacement therapy at the time of testing, who suffered from heart diseases (e.g., heart failure, angina or myocardial infarction), who suffered from uncontrollable hypertension, who suffered from malignant tumor, narrow-angle glaucoma or lung disease, and who suffered from severe renal or hepatic dysfunction.

After the pomegranate extracts were distributed for testing, vital signs and concomitant drugs of the volunteers were checked and Kupperman index was evaluated. Drugs and antioxidants causing side effects, such as facial flushing, were restricted. The volunteers were instructed to store and return the pouches after administration to confirm whether they exactly received the drugs. Four weeks after administration, the vital signs, adverse events and concomitant drugs of the volunteers were examined. Then, laboratory examinations were performed.

Kupperman Index Evaluation

General Kupperman index tests were conducted for the evaluation of menopausal symptoms. Immediately before and after administration, an investigator examined the subjects directly, evaluated collectively the occurrence, intensity and frequency of symptoms for Kupperman index parameters, and recorded the scores on the questionnaire. Based on these results, effects of the inventive pomegranate extracts with high contents of ellagic acid were evaluated. The Kupperman index parameters are shown in Table 2.

TABLE 2

|  | No symptoms (score 0) | Mild (score 1) | Moderate (score 2) | Severe (score 3) |
|---|---|---|---|---|
| Facial flushing | | | | |
| Sweat | | | | |
| Insomnia | | | | |
| Nervousness | | | | |
| Depression | | | | |
| Dizziness | | | | |
| Poor concentration | | | | |
| Joint pain | | | | |
| Headache | | | | |
| Heart palpitation | | | | |
| Colpoxerosis | | | | |

Weighted values were four points for facial flush, two points for sweat, insomnia and nervousness, and one point for depression, dizziness, poor concentration, joint pain, headache, heart palpitation and colpoxerosis. The total score was 51 points.

Test Results (Demographic Information and Kupperman Index Evaluation Results)

The postmenopausal women aged 45-65 were divided into test groups aged 50-53, 54-57, 58-61 and 62-65. Each test group consisted of 10 subjects. The demographic data of the groups are described in Table 3. Kupperman index differences (mean±standard deviation) before and after administration are described in Table 4.

TABLE 3

|  | Aged 50~53 | Aged 54~57 | Aged 58~61 | Aged 62~65 |
|---|---|---|---|---|
| Control | 2 | 4 | 2 | 2 |
| Product A | 2 | 5 | 2 | 1 |
| Product B | 2 | 4 | 2 | 2 |
| Product C | 3 | 3 | 2 | 2 |
| Extract of Example 1 | 2 | 4 | 2 | 2 |

TABLE 4

|  | Control | Product A | Product B | Product C | Inventive extracts |
|---|---|---|---|---|---|
| Kupperman Index | 5.32 ± 0.98 | 8.43 ± 1.09 | 11.87 ± 2.75 | 8.21 ± 2.16 | 25.12 ± 3.48 |

As can be seen from the results in Table 4, the inventive pomegranate pulp extracts containing larger amounts of ellagic acid were much more effective in relieving menopausal symptoms than the other pomegranate extracts containing smaller amounts of ellagic acid.

Example 4

Evaluation of Relieving Effect on Anxiety Disorders, Depression and Attention Deficit Disorders Depending on Ellagic Acid Content The influences of the inventive pomegranate pulp extracts containing large amounts of ellagic acid on anxiety disorders, depression and attention deficit disorders were evaluated by the following methods.

1. Experimental Animals 49 sexually mature female Sprague-Dawley rats weighing 230-280 g were used as experimental animals. Seven rats were not treated, seven rats were sham-operated, and thirty five rats were ovariectomized. After operation, the rats were housed in cages in groups of 3-4 per cage, maintained at a temperature of 20-22° C. on a 12 h light-12 h dark cycle, and given food and water ad libitum. The 24-h intakes of food and water were calculated daily during testing period.

2. Operations

After anesthesia with a mixture of 70 mg/kg of ketamine hydrochloride and 2 mg/kg xylazine, ovaries were excised through a 1-cm incision over both flanks. The same procedure was repeated except that ovaries were not excised (sham operation).

3. Drug Administration and Experiment Plan

The commercially available products (i.e. Products A, B and C) and the inventive pomegranate pulp extracts containing large amounts of ellagic acid were used as test groups. The ellagic acid contents of the test groups are shown in Table 1. The rats were divided into 7 groups as follows. 2 days after operation, the drugs were administered over a period of 4 weeks. Each pomegranate extract was administered orally at a dose of 0.01 ml per g body weight at 9 a.m. daily. 4 weeks after drug administration, the elevated plus maze (EPM) test and forced swim test (FST) were conducted on the test groups. All drugs were forcibly administered orally.

A (n=7): Normal group without ovariectomization and drug administration

B (n=7): Group administered with distilled water after sham operation

C (n=7): Group administered with distilled water after ovariectomization

D (n=7): Group administered with Product A after ovariectomization

E (n=7): Group administered with Product B after ovariectomization

F (n=7): Group administered with Product C after ovariectomization

G (n=7): Group administered with the inventive pomegranate extracts after ovariectomization 4. EPM Test (Examination of Anxiety Disorders)

The behaviors of the rats were observed in a cruciform acrylic maze (open and closed arms, each having a length of 50 cm and a width of 10 cm, central zone having a size of 10 cm×10 cm, and height 50 cm). The experiment was done as described by Daniels et al. Each of the rats was placed at the central zone to direct toward the open arm and was observed for 5 min. The open arm time and the closed arm time were recorded. The rat was judged to enter the arm when four feet thereof were inside the arm. The rat was judged to leave the arm when four feet thereof were outside the arm. The frequencies of entry into the open and closed arms were recorded. From theses frequencies, the frequency of entry into the closed arm was calculated and expressed as a percentage (% closed arm entry). The maze was wiped with 70% ethanol after every experiment to exclude the influence of the rat in the previous experiment.

5. FST (Depression Examination)

5 days after EMP test, FST was implemented according to the method of Porsolt et al. A glass water bath (height=54 cm, diameter=24 cm) was filled with water at 25° C. to a height of 40 cm, and each rat was placed in the water bath for 15 min. On the next day, this experiment was repeated for 5 min. Moving images of all experimental procedure were recorded. A trained third person was allowed to calculate the immobility time.

6. Statistical Analysis

All data was expressed as mean±standard deviation. Statistical comparisons were performed by analysis of variance test. Differences between all groups were done using the Tukey post-hoc tests. Statistical analysis was performed using SPSS 13.0 (SPSS, Inc., Chicago, Ill., USA). A value of $P<0.05$ was considered statistically significant.

7. EPM (Examination of Anxiety Disorders) Test Results

In the EPM test, the % closed arm entries were calculated on the fourth week after drug administration. The % closed arm entries were significantly higher in Group C administered with no pomegranate after ovariectomization, Group D administered with the pomegranate extract including 0.18~0.46 mg/g of ellagic acid, Group E administered with the pomegranate extract including 0.08~0.39 mg/g of ellagic acid and Group F administered with the pomegranate extract including of 0.21~0.40 mg/g ellagic acid than in the normal group. However, the closed arm time and the closed arm entry (%) of Group G administered with the pomegranate extract including 0.8~1.4 mg/g of ellagic acid were significantly lower than those of Group C administered with no pomegranate after ovariectomization ($P<0.05$). The results are shown in Table 5.

TABLE 5

|  | A (n = 7) | B (n = 7) | C (n = 7) | D (n = 7) | E (n = 7) | F (n = 7) | G (n = 7) |
| --- | --- | --- | --- | --- | --- | --- | --- |
| Open Arm Time (s) | 57.1 ± 10.2 | 47.1 ± 11.0 | 33.1 ± 13.5 | 38.3 ± 14.3 | 40.1 ± 17.3 | 32.3 ± 14.3 | 52.0 ± 13.7 |
| Closed Arm Time (s) | 217.7 ± 23.3 | 212.7 ± 25.4 | 232.7 ± 26.0 | 205.6 ± 42.1 | 201.9 ± 38.8 | 245.6 ± 42.1 | 184.1 ± 39.2* |
| Closed Arm Entry (%) | 52.5 ± 11.3* | 63.5 ± 9.6 | 70.4 ± 11.5 | 66.2 ± 10.2 | 63.1 ± 13.4 | 68.2 ± 10.2 | 55.9 ± 6.7* |

In Table 5, statistically significant values compared to Group A are shown in bold, and statistically significant values compared to Group C are shown in asterisks (*).

8. FST (Depression Examination) Results

In the FST, it was confirmed that the 4-week immobility time was increased after ovariectomization but was decreased after administration with the pomegranate extract including 0.8-1.4 mg/g of ellagic acid (Group G). The results are shown in Table 6.

TABLE 6

| Unit (sec) | A (n = 7) | B (n = 7) | C (n = 7) | D (n = 7) | E (n = 7) | F (n = 7) | G (n = 7) |
| --- | --- | --- | --- | --- | --- | --- | --- |
| After 4 weeks | 8.3 ± 9.0* | 10.8 ± 3.6* | 38.6 ± 25.8 | 28.3 ± 9.7 | 20.5 ± 8.6 | 30.2 ± 10.3 | 7.5 ± 6.9* |

In Table 6, statistically significant values compared to Group A are shown in bold, and statistically significant values compared to Group C are shown in asterisks (*).

Example 5

Evaluation of Contents of Other Ingredients in Pomegranate Extracts

In this example, a determination was made as to whether the effects of the inventive pomegranate pulp extracts were simply dependent on the higher ellagic acid concentrations. To this end, the contents of ingredients other than ellagic acid were measured by high-performance liquid chromatography already known in the art. The other ingredients were those known to be present in general pomegranate extracts. The results are shown in Table 7.

TABLE 7

| (Unit: mg/kg) | Product A | Product B | Product C | Inventive extracts |
| --- | --- | --- | --- | --- |
| Daidzein | 0.09 | 0.09 | 0.11 | 0.09 |
| Genistein | 0.08 | 0.14 | 0.07 | 0.11 |
| Quercetin | 0.19 | 0.23 | 0.21 | 0.20 |
| Estriol | 10.17 | 10.02 | 10.34 | 10.40 |
| 17β-estradiol | 0.13 | 0.15 | 0.13 | 0.06 |

As can be seen from the results in Table 7, the ellagic acid contents of the inventive pomegranate extracts were much higher than those of the commercially available products. In contrast, there were no large differences in the contents of the other ingredients between the commercially available products and the inventive extracts. These results clearly show that the effects of the inventive pomegranate pulp extracts with high contents of ellagic acid were not attributed to higher concentrations of the other ingredients.

What is claimed is:

1. A method for treating menopausal symptoms, anxiety disorders, depression, or attention deficit disorders in a woman comprising administering to the woman an effective amount of a pomegranate pulp extract, wherein the content of ellagic acid in the pomegranate pulp extract is at least 0.8 mg/g, and wherein the pomegranate pulp extract is prepared by a method comprising the steps of:

(a) adding one or more polysaccharide-degrading enzymes to a pomegranate pulp; and (b) concentrating the pomegranate pulp by heating to obtain the pomegranate pulp extract.

2. The method according to claim 1, wherein the content of ellagic acid is adjusted to 0.8 to 1.8 mg/g.

3. The method according to claim 1, wherein the content of ellagic acid is adjusted to 0.8 to 1.4 mg/g.

\* \* \* \* \*